United States Patent [19]

Mestroni et al.

[11] 4,290,961

[45] Sep. 22, 1981

[54] PROCESS FOR CATALYTICALLY REDUCING CARBONYL COMPOUNDS

[75] Inventors: Giovanni Mestroni; Grazia Zassinovich; Annamaria Camus, all of Trieste, Italy

[73] Assignee: Montedison S.p.A., Milan, Italy

[21] Appl. No.: 128,049

[22] Filed: Mar. 7, 1980

[30] Foreign Application Priority Data

Mar. 7, 1979 [IT] Italy ............................... 20822 A/79
Feb. 4, 1980 [IT] Italy ............................... 19671 A/80

[51] Int. Cl.³ .................................................. C07J 1/00
[52] U.S. Cl. ............................. 260/397.4; 260/397.5; 568/630; 568/705; 568/706; 568/834; 568/835
[58] Field of Search ...................... 260/397.5, 397.4; 568/630, 705, 706, 834, 835

[56] References Cited

PUBLICATIONS

Tetrahedron Letters No. 45 (1976) pp. 4083–4086.
Journal of Molecular Catalysis, 3 (1977–1978) pp. 385–387.
Inorganic Nuc. Chem. Letters, vol. 15, pp. 235–238.
Jou. of Organo-Metallic Chemistry (1975) 94 C-47, 48.
Chemistry Letters (1973) pp. 239–240.
J.C.S. Chem. Comm. (1972) pp. 1188–1189.
Inorganic Chem., vol. 16, No. 5 (1977) pp. 1220–1225.
Chem. Tech. (Jul. 1975) pp. 421–423.
Tetrahedron Letters, No. 48, pp. 4351–4353.
Tetrahedron Letters, No. 3, (1977) pp. 295–296.
Chem. Comm. 1970, pp. 162–163.
Organic Reactions, vol. II–Adams et al. (1946) pp. 178–182.
J.C.S. Perkin I (1972) pp. 604–606.
Coll. Czech. Chem. Comm. 42 (1977) pp. 2177–2181.
J. Chem. Soc. (C) 1970, pp. 785–791.
J. Org. Chem., vol. 40, No. 13 (1975) pp. 1887–1896.
J. Chem. Soc. (C) (1971) pp. 2652–2656.
J.C.S. Chem. Comm. (1978) pp. 929–930.

*Primary Examiner*—Elbert L. Roberts
*Attorney, Agent, or Firm*—Morgan, Finnegan, Pine, Foley & Lee

[57] ABSTRACT

Catalytic reduction of carbonyl compounds by transfer of hydrogen from alcohols to aliphatic, alicyclic, aromatic, homo- and heterocyclic ketones or aldehydes, catalyzed by rhodium or iridium complexes, characterized in that a primary or secondary alcohol of formula (I) or a glycol:

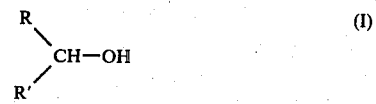

is reacted with a ketonic compound of formula (II):

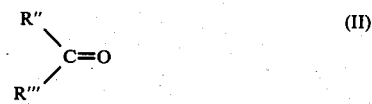

in which R and R' and, respectively, R" and R''', optionally linked with each other according to homo- or heterocycles, indifferently represent a hydrogen atom or a hydrocarbyl group having up to 30 atoms of carbon, also substituted, provided that at least one of symbols R" and/or R''' is different respectively from R and/or R', in the presence of a complex catalyst of rhodium or of iridium selected from those having formulas (III) and (IV):

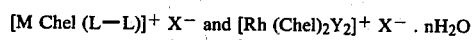

wherein:
 M is selected from Rh and Ir;
 Chel is a chelating bidentate nitrogenous compound;
 L-L is a molecule of a preferably non-conjugated diolefin or two molecules of a monoolefin;
 $X^-$ is an anion selected from amongst $Cl^-$, $Br^-$, $J^-$, $PF_6^-$, $BF_4^-$, $ClO_4^-$, $B(C_6H_5)_4^-$;
 Y is a halogen, preferably it is Cl or Br;
 n is an integer from 0 to 3;

and of a compound selected from amongst mineral alkalis and tertiary amines at a temperature ranging from about 20° C. to the boiling temperature of the reaction mass, preferably in an inert atmosphere.

The products obtained are employed as intermediates for organic syntheses in the field of fine chemicals.

Some terms of the classes of catalysts herein described are to be considered as new in themselves.

22 Claims, No Drawings

PROCESS FOR CATALYTICALLY REDUCING CARBONYL COMPOUNDS

BACKGROUND OF THE INVENTION

The products obtained according to this invention consist respectively of the carbonyl compound hydrogenated to alcohol or of the alcohol dehydrogenated to ketone, or to aldehyde.

This invention, in fact, though described as being specifically directed to the preparation of alcohols according to the abovesaid technology, can be considered, of course, as effective for obtaining ketonic compounds (aldehydes or ketones) from alcohols.

According to a particular aspect of this invention, it is possible to obtain, through said hydrogen transfer reaction, optically active alcohols starting from prochiral ketones.

The products obtained can be usefully employed in a wide field of industrial applications. In fact, they represent active intermediates for organic syntheses in general, with particular possibilities in the field of fine chemicals.

For many of them, the industrial applications are disclosed in literature; for example it is possible to prepare cyclohexanol from cyclohexanone and derivatives thereof, which are interesting compounds in the field of the insecticides, of celluloid, solvents for rubbers, resins, etc., α-phenylethanol from acetophenone for dyes, perfumes, etc.

By the method forming the object of this invention it is possible to obtain, in particular, selective reductions of steroids having carbonyl groups, which are of particular interest in the pharmaceutical field.

For example, from dehydro-epi-androsterone acetate it is possible to obtain the corresponding reduction product of the carbonyl group in position 17.

Methods of preparing alcohols by catalytically transferring a hydrogen atom from a molecule of a primary or secondary alcohol to a molecule of a ketone or of an aldehyde are known.

The reaction results more or less shifted in the desired direction depending on the parameters. Generally it is best operated by using isopropanol as the alcohol donor, due to the facility of separating the acetone deriving from dehydrogenation.

It is known how to use aluminium alkoxides (Meerwein-Ponndorf reaction), but the necessity of operating with a practically stoichiometric ratio renders the proposed method uninteresting from an industrial viewpoint.

Other described catalysts can lead to heterogeneous systems, such as by employing potassium hexachlororuthenate precipitated with sodium formate, and in such case they exhibit the drawbacks which are typical of the reactions in a heterogeneous phase (shorter life of the catalyst, etc.).

Catalyst systems which may permit to operate a homogeneous phase have therefore been studied.

They are essentially based on the use of complexes of transition metals of Group VIII, among which the most studied ones are those deriving from iridium, ruthenium and rhodium.

Therefore, the complex catalysts of formula:

Ir $Cl_3.3DMSO$ (DMSO=dimethylsulphoxide); Ru $Cl_2[P (C_6H_5)_3]_3$ and Rh$[Cl P (C_6H_5)_3]_3$ respectively operating in an acid (HCl), neutral or alkaline, or quite alkaline medium, have been proposed.

Usually, isopropanol or primary alcohols in general, especially benzyl alcohol for the ruthenium catalyst, are described as alcohol donors.

Generally, however, the activity and/or the stereoselectivity obtained in the described substrata, such as the substituted cyclohexanones, is not high. This is a remarkable drawback, since the reaction, as explained hereinbefore, is electively directed to yield fine chemical compounds for which the steric aspect is of the utmost importance. Furthermore, the catalysts described hereinabove provide in general unsatisfactory reaction rates, no doubt lower (even of the order of 100 times) than the ones achievable by using the catalysts according to the present invention, which therefore are remarkably more suitable for industrial uses.

Finally, syntheses of optically active alcohols starting from prochiral ketones through an actual hydrogenation reaction, i.e. a reaction conducted by using molecular hydrogen, have been described.

The reaction is conducted in the presence of rhodium catalysts with chiral binders. Said binders may be phosphines, mono phosphines, diphosphines, ferrocenylphosphines, aminophosphines, diphosphinites, or catalysts based on chiral aminoalcoholic complexes of cobalt are employed.

The catalytic reduction by transfer of hydrogen of an ethylene double bond to α- or β-unsaturated prochiral ketones which become saturated, with phosphinic complex (achiral) catalysts of rhodium and glucides (chiral), has also been described as an alternative method.

The above-mentioned techniques, however, are not directly pertaining to the present invention, because they either employ molecular hydrogen as a reducing agent, or concern the reduction of double bond C=C without selectively affecting the carbonyl group.

The complex catalysts of rhodium and of iridium employed according to this invention are compounds known in themselves and described as having catalytic capabilities in hydrogenation reactions, namely in reactions employing molecular hydrogen as a hydrogenating agent, as explained hereinabove. By consequence such technology has no connection with the one utilized in the present invention.

The present invention represents, in a certain manner, an unexpected overcoming of a prejudice existing in the prior art, according to which the rhodium and iridium complex catalysts of the type described hereinbefore not always exhibited a satisfactory selectivity, or it describes the use of such catalysts in actual hydrogenation reactions with gaseous $H_2$.

THE PRESENT INVENTION

According to the present invention, the preparation of alcohols from aliphatic, alicyclic or aromatic homo- and heterocyclic ketones and aldehydes as hydrogen acceptors, by catalytic transfer of hydrogen from alcohol or glycol donors, which are dehydrogenated to ketones or aldehydes, by using particular complexes of rhodium and of iridium, results particularly effective due to the selectivity of the reaction and the yields obtainable.

Thus, it is an object of this invention to provide a method of catalytically reducing the carbonyl compounds, ketones or aldehydes defined hereinbefore, with rhodium and iridium complexes, such method being simple and economic and particularly selective, mainly directed to the obtainment of a high stereo- and enantio-selectivity by using alcohols and glycols as hydrogen donors.

This and still other objects, which will more clearly appear to those skilled in the art from the following description, are achieved, according to the present invention, by a process for catalytically reducing carbonyl compounds by transfer reaction of hydrogen from alcohols to aliphatic, alicyclic, aromatic homo- and heterocyclic carbonyl compounds (ketones or aldehydes), catalyzed by rhodium and iridium complexes, such process being characterized in that a primary or secondary alcohol of formula (I) or a glycol:

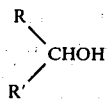
(I)

is reacted with a ketonic compound of formula (II):

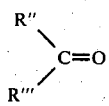
(II)

in which R and R', and respectively R" and R''', also linkable with each other according to homo- and heterocycles, are indifferently a hydrogen atom or a hydrocarbyl group having up to 30 atoms of carbon, optionally substituted, provided that at least one of symbols R" and/or R''' is respectively different from R and/or R', in the presence of a complex catalyst of rhodium and of iridium selected from amongst the ones having the formulas:

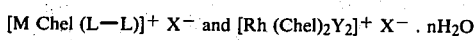

in which: (III)      (IV)

M is selected from Rh and Ir;
Chel is a bidentate nitrogenous compound having a chelating action;
L-L is a molecule of a preferably non-conjugated diolefin or two molecules of a monoolefin;
$X^-$ is an anion selected from amongst $Cl^-$, $Br^-$, $J^-$, $PF_6^-$, $BF_4^-$, $ClO_4^-$, $B(C_6H_5)_4^-$;
Y is a halogen, preferably Cl, Br;
n is an integer from 0 to 3, at a temperature ranging from about 20° C. to the boiling point of the reaction mass, preferably in an inert atmosphere and in the presence of mineral alkalis or of tertiary amines.

Substituting groups for R, R', R", R''' may be, for example, esters, amides, alkoxy groups etc.

The process is particularly suitable for preparing alcohols from the ketones of formula (II) defined hereinbefore, in which at least R" and R''' are different from each other, i.e. they are prochiral ketones, by reaction with the alcohols of formula (I) defined hereinbefore or with a glycol.

In such case, in fact, the products obtained may be in the form of mixtures of optical antipodes.

Therefore, by suitably selecting the chiral bidentate nitrogenous chelating compound it is possible to obtain, with a high yield and a high enantioselectivity, the optically active alcohol or the desired optical antipode.

Furthermore, in the case in which also R and R' in the alcohol are different from each other, namely in the case that a racemic alcohol is employed, at the conclusion of the reaction the reacting mass will result to prevailingly contain the non-utilized optical isomer.

In conclusion, the particular characteristics of enantioselectivity in obtaining the optical antipode alcohols desired from prochiral ketones, can be obtained, according to this process, by using the catalysts and/or the alcohols as defined hereinbefore, containing asymmetrical atoms, i.e. chiral in their turn, as better explained later on.

Finally, it is possible, to improve the enantioselectivity effect, to introduce into the catalytic system, as an auxiliary component thereof, a compound consisting, in its turn, of chiral amines.

The reaction is usually conducted in the absence of actual solvents, the alcohol of formula (I) or the glycol in excess acting also as a solvent. Anyhow the reaction is consistent with conventional inert solvents such as toluene, benzene, methanol, $H_2O$ etc., also in admixture.

The catalysts are employed, as illustrated hereinbefore, in the presence of small amounts of mineral alkalis, preferably selected from amongst NaOH, KOH, LiOH, $NaHCO_3$, in a molar ratio preferably ranging from 0.1 to 200 in respect of 1 mole of catalyst.

As an alternative it is possible to employ tertiary amines, such as triethylamine, dimethylbenzylamine, etc.

The choice of the optimum ratio of the mineral alkali or of the amine to the Rh or Ir catalyst utilized is of considerable importance for purposes of electively directing the hydrogen transfer to the obtainment of the desired stereoisomer.

Such choice can be made according to the nature of the substratum, of the catalyst and of the employed mineral alkali or of the amine etc.

Therefore, as an example, in the case of cyclohexanones, it is possible to direct the reaction to the obtainment of the stereoisomers having group OH in the equatorial position by decreasing the concentration of the mineral alkali, the concentration of the catalyst being constant.

As a further principle for the choice of the catalyst it is to be pointed out that, for purposes of the stereoselectivity of the reaction in respect of the desired compound, rhodium and iridium exert a substantially complementary action. In other words, as an example, when substituted cyclohexanones are employed as substrata, the use of iridium or of rhodium as metal predominantly and selectively leads to alcohols having the hydroxyl function respectively in the equatorial position for iridium, in the axial position for rhodium.

Better results are achieved by subjecting the rhodium catalyst of formula (IV) to a preventive heating "in situ", namely in the alcohol donor or in the solvent before introducing the carbonyl compound, in the presence of the abovesaid mineral alkalis or tertiary amines and for stretches of time ranging from a few minutes to about 1 hour. In like manner the catalysts of formula (III) to provide the optimum catalytic activity if they are subjected in their turn, before undergoing said heating, to activation by oxidation in the air and/or in molecular oxygen or $H_2O_2$, etc. This is a preferred procedure, but not an absolutely necessary one; for example, if the olefin is 1,5-hexadiene, such procedure is even superfluous.

The reaction can be schematically represented by the following equation:

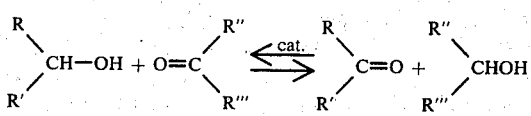

in which the symbols have the meanings already specified herein.

The reaction is selectively shifted in the preferred direction depending on the parameters (temperature, catalysis, etc.) and on the conduction conditions, for example by substracting a proper chemical species etc.

The complexes of rhodium and or iridium employed as catalysts according to the present invention are prepared, in their turn, according to known or conventional techniques.

For example, the complex of type (III) of formula [Rh Chel (1,5-hexadiene)]PF$_6$ in which the chelating compound is selected from among 2,2'-dipyridyl(bipy), 4,4'-dimethyl-2,2'-dipyridyl, 1,10-phenanthroline, 5,6-dimethyl-1,10-phenanthroline, etc., can be synthetized by addition of the chelating compound to a deaerated methanol solution of [Rh-hexadiene-Cl]$_2$, followed by an optional treatment with a salt containing the desired anion other than chlorine.

The complex of formula [Rh (Chel)$_2$Cl$_2$]Cl of type (IV), in which the chelating compound is, for example, 2,2'-dipyridyl (bipy), can be prepared starting from an aqueous solution of RhCl$_3$.3H$_2$O, to which a hot ethanol solution of the chelating compound in a molar ratio of 1:2 is added. The resulting reaction mixture, heated to 60° C., is added with a small amount of chlohydrated hydrazine and is heated to boiling for 3 minutes. After cooling of the solution, the desired product precipitates in the form of a yellow solid.

In like manner, the iridium complex of formula [Ir Chel (L-L)]Cl of type (III), in which the chelating compound is, for example, 3,4,7,8-tetramethyl-1,10-phenanthroline and L-L is 1,5-cyclooctadiene (COD), can be prepared starting from a deaerated solution of [Ir-CODCl]$_2$ in methylene chloride by addition of the chelating compound in a slight excess and by successive precipitation with ethyl ether. All these are known or conventional techniques.

As illustrated hereinbefore, the complex catalysts of rhodium and of iridium employed according to this invention have formulas (III) and (IV), in which, in particular, the nitrogeneous bidentate chelating compound (Chel) is preferably selected from amongst 2,2'-dipyridyl (bipy), 3,3'-dimethyl-2,2'-dipyridyl, 4,4'-dimethyl-2,2'-dipyridyl, 1,10-phenanthroline, 5,6-dimethyl-1,10-phenanthroline, 4,7-dimethyl-1,10-phenanthroline, 3,4,7,8-tetramethyl-1,10-phenanthroline, 4,7-diphenyl-1,10-phenanthroline.

Or it is possible to employ the chelating compounds of formulas (V) and (VI), obtained from pyridin-2-aldehyde or from 2-acyl-pyridin, also substituted (by alkyls, alkoxyls), by condensation with alkylaryl primary amines, hydrazines, also N,N-substituted, hydroxylamine (V), or by condensation of alpha-diketones or alpha-dialdehydes, such as diacetyl and glyoxal, with the abovesaid amines etc. (VI):

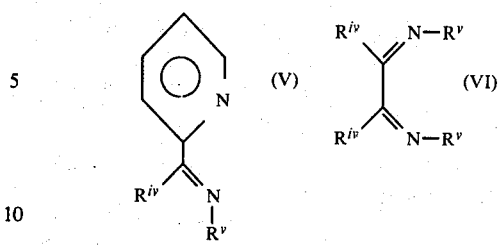

in which groups R$^{iv}$, like or unlike one another, are selected from amongst H, alkyl and aryls, and groups R$^v$, like or unlike one another, are selected from amongst OH, NH$_2$, alkyls and aryls, all having up to 30 carbon atoms, also containing functional groups such as carboxyl, ester, amide, groups etc.

The aforesaid chelating compounds of formulas (V) and (VI) are particularly suitable for obtaining chiral alcohols from prochiral ketones.

Particularly effective chelating compounds, in this regard, have proved to be the chelating compounds of formulas (V) and (VI) in which groups R$^v$, like or unlike one another, are groups as defined hereinbefore containing chiral centres, i.e. at least an optically active atom, such as for example:

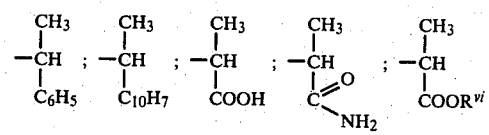

in which R$^{vi}$=CH$_3$, iso C$_3$H$_7$ etc.

In formulas (V) and (VI) groups R$^{iv}$ and R$^v$ can be also connected with one another according to homo- or heterocycles.

The synthesis of the rhodium- and of the iridium-catalysts containing the said optically active chiral chelating compounds is described, for example, in Journal of Organometallic Chemistry, 133 (1977), 377–384. 2-pyridinalphenylethylimine (PPEI), 2-pyridinalnaphthylethylimine, etc. have proved to be effective chelating compounds.

Nevertheless, some terms of the abovesaid group of iridium and rhodium catalysts containing chelating compounds of formula (V) or (VI) are to be considered as new in themselves.

The preferably non-conjugated diolefin is selected from amongst 1,5-hexadiene, norbornadiene and 1,5-cyclooctadiene(cis-cis); the monoolefin is cyclooctene or ethylene; anion X$^-$ has been already defined.

Finally, the catalyst according to this invention can be also prepared directly "in situ" in the reaction medium by adding the selected chelating compound to the halogenated olefinic complex of rhodium or of iridium: for example to [Rh-1,5-hexadiene-Cl]$_2$ or to [Rh(cyclooctene)$_2$Cl]$_2$, dipyridyl is added in the desired ratio, whereupon it is activated as explained hereinbefore.

According to this invention, the catalyst is employed in amounts which may vary over a wide range.

Advantageous results are obtained by employing, for each mole of carbonyl compound, amounts of catalyst ranging from $1 \times 10^{-2}$ to $1 \times 10^{-6}$ moles.

The complex catalysts of rhodium and of iridium of the present invention are employed according to conventional techniques in a medium which is basic, as specified hereinbefore, due to mineral alkalis or tertiary amines.

Suitable reaction mediums are preferably the alcoholic solutions, consisting of the alcohol donor (I) or of the glycol in excess which act as the reaction medium.

The concentration of the carbonyl compound in the reaction mass is not critical for the purpose of a correct conduction of the reaction; values of from 10 to $10^{-3}$ moles per liter are effective.

The reaction is conducted according to a molar ratio of the reagents varying over a wide range; practically optimum results are obtainable with values of the molar ratio between alcohol donor and acceptor carbonyl compound ranging from 1:1 to 20:1, the alcohol in excess being utilized as a solvent reaction medium.

The concentration of the catalyst in the reaction mass is practically comprised between $10^{-1}$ and $10^{-6}$ moles per liter of reaction mass.

The reduction or dehydrogenation reaction according to this invention is conducted at ambient pressure and preferably in an inert atmosphere, such as nitrogen, argon, etc.

Temperatures ranging approximately from 20° to 200° C. are possible up to the boiling temperature of the solution.

Reducible carbonyl compounds according to this invention are in particular, among the ketonic ones: cyclohexanone, 4-terbutyl-cyclohexanone, 3-methyl-cyclohexanone, 4-methyl-cyclohexanone, 2-methyl-cyclohexanone, acetophenone, propiophenone, methyl-iso-butyl-ketone, isobutyrophenone, dihydrocarvone, benzophenone, benzyl, dehydro-epi-androsterone acetate, 3-oxosteroids, etc.

Therefore also compounds having more than one carbonyl function (benzyl) are reducible, said functions being in such case reduced.

Among the aldehydes: benzaldehyde, p-methoxybenzaldehyde. Effective alcohol donors are for example: isopropyl alcohol, ethyl alcohol, 2-butyl alcohol, benzyl alcohol, etc.; as glycol, 1,2-cyclododecandiol. Products of the commercial type are employable.

The product is then separated according to conventional techniques. Practically it is a question of separating the solvent by distillation, while the high-boiling part consists generally quantitatively of the alcohol, etc.

According to an effective embodiment of the invention it is operated in practice as follows.

The optional solvent and the alcohol donor and then the desired amount of catalyst or of oxidized catalyst and of base in the proper ratios are introduced into a reactor equipped with feeding systems of the reagents and thermoregulated. The catalyst is then activated by heating, whereupon the carbonyl compound is added, in the prefixed ratio, in a nitrogen stream, heating to the temperature and for the time fixed. At the conclusion of the reaction, controlled for example by gas-chromatography, the product is isolated according to conventional techniques.

Due to the simple and mild operative conditions, the process results particularly advantageous.

A further advantage consists in having the possibility of conducting the selective reduction of the carbonyl compounds also in the presence of olefinic bonds, such feature being of particular interest for the industry.

Furthermore, the process according to the present invention permits to obtain—thanks to the higher activity of the catalysts in respect of the phosphinic catalysts of the art-higher conversions, exceeding 98%, in shorter times and with higher substratum/catalyst ratios, even of the order of 1:150,000.

By using chiral nitrogenous chelating compounds it is possible, at last, to obtain high yields and enantioselectivities in the alcohols derived from ketones, with better productive capacities per unit of time and per catalytic unit.

The present invention will be now further described in the following examples, which are given however for merely illustrative purposes.

For clearness' sake, the symbols used are the following: Me=methyl, phen=phenanthroline, "bipy" means 2,2'-dipyridyl, COD=1,5-cyclooctadiene, PPEI=2-pyridinalphenylethylimine, NBD=norbornadiene. e.e.-=enantiomeric excess.

EXAMPLE 1

13.2 mg ($2 \times 10^{-5}$ moles) of [Rh(4,7 Me$_2$-phen)$_2$Cl$_2$]Cl.2H$_2$O were dissolved in 50 ml of aqueous isopropanol (0.2% of H$_2$O) containing 100 mg of KOH.

The resulting solution was heated at reflux for 5 minutes in a nitrogen stream, whereupon 10 ml of cyclohexanone ($9.58 \times 10^{-2}$ moles) were added.

It was heated at reflux in a nitrogen atmosphere for 90 minutes. The gaschromatographic analysis of the solution revealed a conversion to cyclohexanol of 85%. Ratios:
[cyclohexanone]/[cat.]=4790; [KOH]/[cat.]=89.

EXAMPLE 2

16.5 mg ($2.5 \times 10^{-5}$ moles) of [Rh(4,7Me$_2$-phen)$_2$Cl$_2$]Cl.2H$_2$O dissolved in 50 ml of aqueous isopropanol (0.2% of H$_2$O) containing 100 mg of KOH were heated at reflux in a nitrogen stream for 5 minutes.

After addition of 5 g of 4-terbutyl-cyclohexanone, it was heated at reflux in a nitrogen atmosphere for 90 minutes.

The gaschromatographic analysis of the solution revealed a conversion to cis-4-terbutyl-cyclohexanol+-trans-4-terbutyl-cyclohexanol of 99%.

The ratio between cis isomer and trans isomer resulted to be cis/trans=4. Ratios:
[4-terbutylcyclohexanone]/[cat.]=1300; [KOH]/[cat.]=71.

EXAMPLE 3

16.5 mg ($2.5 \times 10^{-5}$ moles) of [Rh(4,7Me$_2$-phen)$_2$Cl$_2$]Cl.2H$_2$O dissolved in 50 ml of aqueous isopropanol (0.2% of H$_2$O) containing 100 mg of KOH were heated at reflux in a N$_2$ stream for 5 minutes. 5 ml of 3-methyl-cyclohexanone were then added and it was heated at reflux in a nitrogen atmosphere for 90 minutes.

The gaschromatographic analysis of the solution revealed a conversion to trans-3-methylcyclohexanol+-cis-3-methylcyclohexanol of 94%. The ratio between trans isomer and cis isomer was trans/cis=4.5. Ratios:
[3-methyl-cyclohexanone]/[cat.]=1630; [KOH]/[cat.]=71.

EXAMPLE 4 (without activation with oxygen)

10 mg ($2.5 \times 10^{-5}$ moles) of [Rh 4,7 Me$_2$phen(1.5-hexadiene)]Cl dissolved in 50 ml of isopropanol-H$_2$O (0.2%) containing 100 mg of KOH were heated at reflux in a nitrogen stream for 5 minutes. 5 g of 4-terbutyl-cyclohexanone were then added and it was heated at reflux in a nitrogen atmosphere for 90 minutes. The gaschromatographic analysis of the solution revealed a conversion to cis-4-terbutylcyclohexanol+trans-4-terbutyl-cyclohexanol of 92%. The ratio between cis isomer and trans isomer was: cis/trans=2.4. Ratios: [substratum]/[cat.]=1300; [KOH]/[cat.]=71.

EXAMPLE 5

15 mg of ($2.5\times10^{-5}$ moles) of [Rh(4,4'-Me$_2$-bipy)$_2$Cl$_2$]Cl.2H$_2$O dissolved in 50 ml of isopropanol-H$_2$O (0.2%) containing 100 mg of KOH were heated at reflux in a nitrogen stream for 5 minutes. After addition of 5 of 4-terbutylcyclohexanone it was heated at reflux in a nitrogen stream for 90 minutes. The gaschromatographic analysis of the solution revealed a conversion to cis-4-terbutyl-cyclohexanol+trans-4-terbutyl-cyclohexanol of 85%. The ratio between cis isomer and trans isomer was: cis/trans=1.5. Ratios: [substratum]/[cat.]=1300; [KOH]/[cat.]=71.

EXAMPLE 6

10 mg of [Ir phen COD] Cl ($2\times10^{-5}$ moles) were dissolved in 50 ml of isopropanol-H$_2$O (2%). The solution so obtained was oxidized with air and successively treated at reflux for 10 minutes in the presence of 100 mg of KOH in a nitrogen atmosphere. 6.5 ml of cyclohexanone were then added and it was heated at reflux for 60 minutes in a nitrogen atmosphere. The solution, subjected to gaschromatographic analysis, revealed a conversion to cyclohexanol of 94%. Ratios: [substratum]/[cat.]=3117; [KOH]/[cat.]=89.

EXAMPLE 7

11 mg of [Ir(3,4,7,8 Me$_4$phen)COD[Cl ($2\times10^{-5}$ moles) were dissolved in 50 ml of isopropanol-H$_2$O (2%). The resulting solution was oxidized with air and successively treated at reflux for 20 minutes in the presence of 10 mg of KOH. After addition of 10 ml of cyclohexanone it was heated at reflux for 30 minutes in a nitrogen atmosphere. The solution, subjected to gas-chromatographic analysis, revealed a conversion to cyclohexanol of 90%. Ratios: [substratum]/[cat.]=4788; [KOH]/[cat.]=9.

EXAMPLE 8

0.55 mg of [Ir(3,4,7,8 Me$_4$phen)COD]Cl ($1\times10^{-6}$ moles) were dissolved in 50 ml of isopropanol-H$_2$O (1.4%). The solution so obtained was oxidized with air and subsequently treated at reflux for 50 minutes in the presence of 2.24 mg of KOH in an argon atmosphere. 4 ml of cyclohexanone were then added and it was heated at reflux for 3 hours in an argon atmosphere. The gaschromatographic analysis of the solution revealed a conversion to cyclohexanol of 95%. Ratios: [substratum]/[cat.]=38300; [KOH]/[cat.]=40.

EXAMPLE 9

0.275 mg of [Ir(3,4,7,8 Me$_4$phen)COD]Cl ($5\times10^{-7}$ moles) were dissolved in 50 ml of isopropanol-H$_2$O (0.6%). The solution so obtained was oxidized with air and successively treated at reflux for 50 minutes in the presence of 2.24 mg of KOH in an argon atmosphere. After addition of 4 ml of cyclohexanone it was heated at reflux for 8 hours in an argon atmosphere. The gaschromatographic analysis of the solution revealed a conversion to cyclohexanol of 98%. Ratios: [substratum]/[cat.]=76600; [KOH]/[cat.]=80.

EXAMPLE 10

0.275 mg of [Ir(3,4,7,8 Me$_4$phen)COD]Cl ($5\times10^{-7}$ moles) were dissolved in 50 ml of isopropanol-H$_2$O (0.6%). The resulting solution was oxidized with air and successively treated at reflux for 50 minutes in the presence of 2.24 mg of KOH in an argon atmosphere. 8 ml of cyclohexanone were then added and it was heated at reflux for 19 hours in an argon atmosphere. The gaschromatographic analysis of the solution revealed a conversion to cyclohexanol of 98.5%. Ratios: [substratum]/[cat.]=153200; [KOH]/[cat.]=80.

EXAMPLE 11

11 mg of [Ir(3,4,7,8 Me$_4$phen)COD]Cl ($2\times10^{-5}$ moles) were dissolved in 50 ml of isopropanol-H$_2$O (2%). The solution so obtained was oxidized with air and then treated at reflux for 10 minutes in the presence of 10 mg of KOH. 5 g of 4-terbutylcyclohexanone were then added, going on heating at reflux. After 30 minutes the gaschromatographic analysis of the solution revealed a conversion to cis-4-terbutyl-cyclohexanol+4-trans-terbutyl-cyclohexanol of 99.5%. The ratio between the trans isomer and the cis isomer was: trans/cis=4. Ratios: [substratum]/[cat.]=1630; [KOH]/[cat.]=9. Similar results were obtained by using 5 mg of KOH: a conversion of 90% in 60 minutes, and by using 2.5 mg of KOH: a conversion of 90% in 120 minutes.

EXAMPLE 12

2.2 mg ($4\times10^{-6}$ moles) of [Ir(3,4,7,8 Me$_4$phen)-COD]Cl were oxidized with molecular oxygen in 50 ml of isopropanol-H$_2$O (2%). It was heated at reflux in a nitrogen atmosphere for 10 minutes in the presence of 20 mg of KOH. After addition of 5 g of terbutyl-cyclohexanone it was heated at reflux in a nitrogen atmosphere for 6 hours. A conversion of 77% was obtained. Ratios: [substratum]/[cat]=8150; [KOH]/[cat.]=89.

EXAMPLE 13

10 mg of [Ir(4,4' Me$_2$bipy)COD]Cl ($2\times10^{-5}$ moles) were dissolved in 50 ml of isopropanol-H$_2$O (2%). The solution so obtained was oxidized with air and successively treated at reflux for 10 minutes in the presence of 100 mg of KOH in a nitrogen atmosphere. 5 g of 4-terbutyl-cyclohexanone were then added. After 60 minutes the gaschromatographic analysis of the solution revealed a conversion to cis-4-terbutyl-cyclohexanol+trans-4-terbutyl-cyclohexanol of 99%. The ratio between trans isomer and cis isomer was: trans/cis=4. Ratios: [substratum]/[cat.]=1630; [KOH]/[cat.]=89.

EXAMPLE 14

1 mg ($2\times10^{-5}$ moles) of [Ir(3,4,7,8 Me$_4$phen)-COD]Cl oxidized with air in 50 ml of isopropanol-H$_2$O (1%) were treated with 0.56 ml of an aqueous solution of KOH (100 mg in 50 ml of H$_2$O) and successively heated at reflux for 1 hour. 5 g of 4-terbutyl-cyclohexanone were then added and it was heated at reflux for 30 minutes. The gaschromatographic analysis revealed a conversion of 100% and a trans/cis ratio=22.1 (95.5% of trans isomer). By addition of water and vacuum removal of the isopropanol and of the acetone which had formed, the reaction product 4-terbutyl-cyclohexanol was isolated. Ratios: [KOH]/[cat.]=1; [substratum]/[cat.]=1630. This example points out the possibility of obtaining, with a ratio KOH/cat.=1, the reduction of 4-terbutyl-cyclohexanone with a high stereoselectivity. In fact, when repeating the test under the same operative conditions as employed before, higher amounts of KOH were used, precisely 5.6 ml and 11.2 ml of aqueous solution, corresponding to a KOH/cat. ratio equal to 5 and 10, respectively. Equal conversions of 100% were obtained, while the trans/cis ratios decreased to 4.5 and 4, respectively.

EXAMPLE 15 (reduction of substituted cyclohexanones)

16 mg of [Rh(4,7 Me$_2$phen)$_2$Cl$_2$]Cl.2H$_2$O (2.5×10$^{-5}$ moles) were treated in 50 ml of hot deaerated isopropanol with 100 mg of KOH. After 3 minutes, 2 ml of 4-methyl-cyclohexanone were added in a nitrogen stream and it was heated at reflux for 20 minutes. A conversion to 4-methyl-cyclohexanols of 100% was obtained, the ratio between cis-4-methyl-cyclohexanol and trans-4-methyl-cyclohexanol being 2.7. Ratios: [substratum]/[cat.]=650; [KOH]/[cat.]=72. The test was repeated using 3-methyl-cyclohexanone as a substratum. The following values were obtained: conversion of 96% to 3-methyl-cyclohexanols, the ratio between trans-3-cyclohexanol and cis-3-methyl-cyclohexanol being 7. Ratios: [substratum]/[cat.]=650; [KOH]/[cat.]=72. The test was repeated once again using 2-methyl-cyclohexanone as a substratum. After a 45-minute reaction the following values were obtained: conversion to 2-methyl-cyclohexanols of 99%, the ratio between cis-2-methyl-cyclohexanol and trans-2-methyl-cyclohexanol being 99. Ratios: [substratum]/[cat.]=650; [KOH]/[cat.]=72.

EXAMPLE 16 (reduction of substituted cyclohexanones)

11 mg of [Ir(3,4,7,8 Me$_4$phen)COD]Cl (2×10$^{-5}$ moles) were oxidized with air in 50 ml of isopropanol-H$_2$O (1%) and successively treated in a nitrogen stream with 0.6 ml of an aqueous solution of KOH (2×10$^{-5}$ moles). It was heated at reflux for 1 hour, whereupon 2 ml of deaerated 4-methyl-cyclohexanone were added and it was heated at reflux for 2 hours. The following values were obtained: conversion of 93% to 4-methyl-cyclohexanols with a ratio between trans-4-methyl-cyclohexanol and cis-4-methyl-cyclohexanol of 4.5. Ratios: [substratum]/[cat.]=800; [KOH]/[cat.]=1. The test was repeated using 3-methyl-cyclohexanone as a substratum. After a 60-minute reaction the following values were obtained: conversion of 100% to 3-methyl-cyclohexanols, the ratio between cis-3-methyl-cyclohexanol and trans-3-methyl-cyclohexanol being 9.3. From a comparison between the selectivity ratios specified in example 15, in which a rhodium catalyst was utilized, and the corresponding values of this example, in which an iridium catalyst was used, it can be inferred that, the substratum 4-methyl-cyclohexanone being the same, one has passed from a cis/trans value=2.7 with rhodium to a trans/cis value=4.5 with iridium and similarly for 3-methyl-cyclohexanone from 7 to 9.3. The selectivity complementary action of the catalysts results evident.

EXAMPLE 17 (recovery and recycle of the catalyst)

11 mg of [Ir(3,4,7,8 Me$_4$phen)COD]Cl (2×10$^{-5}$ moles) were oxidized with air in 50 ml of isopropanol-H$_2$O (1%) and successively treated in a nitrogen stream with 0.56 ml of an aqueous solution of KOH containing 2×10$^{-5}$ moles of KOH. After heating at reflux for 1 hour, 5 g of 4-terbutyl-cyclohexanone were added in a nitrogen stream and it was then heated at reflux for 60 minutes. The following values were obtained: conversion to 4-terbutyl-cyclohexanols of 100%, with a ratio between trans-4-terbutyl-cyclohexanol and cis-4-terbutyl-cyclohexanol=21. Ratios: [substratum]/[cat.]=1630; [KOH]/[cat.]=1. By addition of water and removal of isopropanol, 4-terbutyl-cyclohexanols precipitated, which were isolated by filtration, with a yield>90%. The mother liquors were hot concentrated to a volume of 2 ml and then diluted with isopropanol to 50 ml 20 mg of KOH ([KOH]/[cat.]=20) were added to the solution so obtained, whereupon it was heated at reflux for 10 minutes; 5 g of 4-terbutyl-cyclohexanone were then added and heating was carried on for 45 minutes. A conversion to 4-terbutyl-cyclohexanols equal to 99.6% was obtained.

EXAMPLE 18

33 mg of Ir[(3,4,7,8 Me$_4$phen)COD]Cl were oxidized with air in 150 ml of isopropanol-H$_2$O (2%). After addition of 100 mg of KOH ([KOH]/[cat.]=30) it was heated at reflux for 3 hours. 15 ml of acetophenone were then added. The gaschromatographic analysis revealed a conversion to 1-phenylethanol of 96% in 45 minutes, with a ratio between substratum and catalyst=2140.

EXAMPLE 19

Example 18 was repeated using, as a substratum, 15 ml of methyl-isobutylketone. The gaschromatographic analysis revealed a conversion to the corresponding alcohol equal to 52% in 60 minutes. Acetone was removed by distillation as it formed in order to facilitate the thermodynamic course of the reaction.

EXAMPLE 20

2.75 mg of [Ir(3,4,7,8 Me$_4$phen)COD]Cl (5×10$^{-6}$ moles) were dissolved in 50 ml of isopropanol-H$_2$O (1%). The resulting solution was oxidized with air and successively treated at reflux for 50 minutes in the presence of 2.24 mg of KOH in an argon atmosphere. 3 g of benzophenone were then added and it was heated at reflux for 165 minutes.

The gaschromatographic analysis of the solution revealed a conversion to diphenylcarbinol of 95.5%. Ratios: [substratum]/[cat.]=3300; [KOH]/[cat.]=8.

EXAMPLE 21

2.75 mg of [Ir(3,4,7,8 Me$_4$phen)COD]Cl (5×10$^{-6}$ moles) were dissolved in 50 ml of isopropanol-H$_2$O (1%). The solution so obtained was oxidized with air and successively treated at reflux for 50 minutes in the presence of 2.24 mg of KOH in an argon atmosphere. 3.5 g of benzyl were then added and it was heated at reflux for 120 minutes.

1,2-diphenyl-ethanediol was precipitated by cooling and identified on the basis of its melting point and infrared spectrum. Ratios: [substratum]/[cat.]=3300; [KOH]/[cat.]=8.

EXAMPLE 22

5 mg of Ir phen COD Cl (1×10$^{-5}$ moles) were dissolved in 50 ml of isopropanol-H$_2$O (1%). The resulting solution was oxidized with air and then kept at room temperature for 6 hours in the presence of 50 mg of KOH in an argon atmosphere. After addition of 2 ml of cyclohexanone, it was reacted at room temperature for 6 days. The gaschromatographic analysis of the solution revealed a conversion to cyclohexanol of 34%. Ratios: [substratum]/[cat.]=1600; [KOH]/[cat.]=89.

EXAMPLE 23

6.8 mg of [Ir(4,7 (C$_6$H$_5$)$_2$phen)COD]Cl (1×10$^{-5}$ moles) were dissolved in 50 ml of isopropanol-H$_2$O (1%). The resulting solution was oxidized with air and then kept at room temperature for 6 hours in the presence of 5 mg of KOH in an argon atmosphere. 2 ml of cyclohexanone were then added, whereupon it was reacted at room temperature for 6 days. The gaschromatographic analysis of the solution revealed a conversion to cyclohexanol of 30%. Ratios: [substratum]/[cat.]=1600; [KOH]/[cat.]=9.

EXAMPLE 24

5.5 mg of [Ir(3,4,7,8 Me$_4$ phen)COD]Cl (1×10$^{-5}$ moles) were dissolved in 50 ml of isopropanol-H$_2$O (2%). The solution so obtained was oxidized with air and successively treated at reflux for 50 minutes in the presence of 2.24 mg of KOH in an argon atmosphere. After addition of 2 ml of dihydrocarvone, it was heated at reflux for 120 minutes.

The gaschromatographic analysis revealed a conversion to dihydrocarveol of 90%. Ratios: [substratum]/[cat.]=1300; [KOH]/[cat.]=5.

EXAMPLE 25

11 mg of [Ir(3,4,7,8 Me$_4$ phen)COD]Cl (2×10$^{-5}$ moles) were dissolved in 50 ml of isopropanol-H$_2$O (1%). The solution so obtained was oxidized with air and successively treated at reflux in the presence of 300 mg of dehydroepiandrosterone-acetate and of 5 mg of KOH. It was then heated at reflux for 4 hours. By cooling and dilution with water, a white crystalline solid precipitated which, on the basis of its melting point and infrared spectrum, was identified as dehydroepiandrostan-17-ol.

EXAMPLE 26

24.4 mg of [Ir(PPEI)COD]ClO$_4$(+) (4×10$^{-5}$ moles) were dissolved in 100 ml of sec.-butanol. The resulting solution was oxidized with air and successively treated at reflux for 30 minutes in the presence of 8 mg of KOH in a nitrogen atmosphere. 4.8 ml of acetophenone were then added and it was heated at reflux for 60 minutes. The gaschromatographic analysis of the solution revealed a conversion to 1-phenylethanol of 85%. The polarimetric analysis revealed an e.e. of 9% in 1-phenylethanol (+).

EXAMPLE 27

5.5 mg of [Ir(3,4,7,8 Me$_4$ phen)COD]Cl (1×10$^{-5}$ moles) were dissolved in 50 ml of anhydrous ethanol. The resulting solution was oxidized with air and subsequently treated at reflux for 15 minutes in the presence of 0.56 mg of KOH in an argon atmosphere. 2.5 g of 4-terbutyl-cyclohexanone were then added and it was heated at reflux for 90 minutes.

The gaschromatographic analysis of the solution revealed a conversion to 4-terbutyl-cyclohexanols (cis+-trans) of 10%, with a trans/cis ratio=10. Ratios: [substratum]/[cat.]=1600; [KOH]/[cat.]=1.

EXAMPLE 28

11 mg (2×10$^{-5}$ moles) of [Ir(3,4,7,8 Me$_4$ phen)-COD]Cl were oxidized with air in 50 ml of isopropanol-H$_2$O (1%), and then treated with 0.5 ml of an aqueous solution of KOH (100 mg in 50 ml) and successively heated at reflux for 15 minutes. 0.5 ml of p. methoxy-benzaldehyde were added. The gaschromatographic analysis carried out after 10 minutes revealed a conversion to p. methoxy-benzyl-alcohol of 84%.

EXAMPLE 29

2.75 mg of [Ir(3,4,7,8 Me$_4$ phen)COD]Cl (5×10$^{-6}$ moles) were dissolved in 50 ml of isopropanol. The resulting solution was oxidized with air and successively treated at reflux for 50 minutes in the presence of 1.1 mg of KOH in an argon atmosphere. After addition of 2 ml of benzaldehyde, it was heated at reflux for 1 hour in an argon atmosphere. The gaschromatographic analysis of the solution revealed a conversion to benzyl alcohol of 24%. Ratios: [substratum]/[cat.]=3950; [KOH]/[cat.]=3.5.

EXAMPLE 30

[Ir (PPEI) COD]$^+$ClO$_4^-$ (+) 12.2 mg (2×10$^{-5}$ moles) were put into 50 ml of isopropanol and oxidized with air for 4 hours. The solution, after having been oxidized, degasified at room temperature and treated in an inert atmosphere with 8.76 ml of an isopropanol solution of KOH (8 mg), was allowed to react under stirring at room temperature for 60 minutes. 2.4 ml of deaerated acetophenone were added to such solution. After a 140-hour reaction at room temperature, the conversion to phenylethanol (+) was of 36.4% with an e.e. of 4.5%. Ratios: [substratum]/[cat.]=1000; [KOH]/[cat.]=7.2.

EXAMPLE 31

24.4 mg of [Ir(PPEI)COD]$^+$ClO$_4^-$ (+) (4×10$^{-5}$ moles) (PPEI=2-pyridinal-phenylethylimine; COD=-cis cis 1-5 cyclooctadiene), suspended in 1 ml of isopropanol were oxidized with air for 4 hours. The resulting yellow solution was degasified for 20 minutes at reflux in a nitrogen stream and treated with 3.75 ml of a deaerated isopropanol solution of KOH (8 mg of KOH). After a 30-minutes reduction in a nitrogen stream, 4.8 ml of deaerated acetophenone were added. After a 120-minute reaction, a conversion to 1-phenylethanol (+) of 91.2% and an e.e. of 13.6% were obtained. The polarimetric determination was effected on the hydrogenation product distilled at reduced pressure. Ratios: [substratum]/[cat.]=1000; [KOH]/[cat.]=3.56.

EXAMPLE 32

24.4 mg (4×10$^{-5}$ moles) of [Ir(PPEI)COD]$^+$ClO$_4^-$ (−) suspended in 100 ml of isopropanol were oxidized with air for 4 hours. The resulting yellow solution was degasified for 20 minutes at reflux in a nitrogen stream and treated with 1.94 ml of an isopropanol solution of KOH (4 mg of KOH). After a 30-minute reduction in a nitrogen stream, 5.3 ml of deaerated propiophenone were added. After a 240-minute reaction, a conversion to phenylpropanol (−) of 98.5% with an e.e. of 25.07% was obtained. The polarimetric determination was effected on the hydrogenation product distilled at reduced pressure. Ratios: [substratum]/[cat.]=1000; [KOH]/[cat.]=1.8.

EXAMPLE 33

12.2 mg ($2 \times 10^{-5}$ moles) of [Ir(PPEI)COD]$^+$ClO$_4^-$ (+) were suspended in 50 ml of isopropanol and oxidized with air for 4 hours. The yellow limpid solution so obtained was degasified for 20 minutes at reflux under a nitrogen stream and then treated with 2.7 ml of a deaerated isopropanol solution of KOH (2 mg of KOH). The solution was preliminarily reduced for 30 minutes in a N$_2$ stream at reflux and then treated with 2.56 ml of deaerated propiophenone. After 60 minutes the reaction was stopped, obtaining a conversion to phenylpropanol (+) of 57.3% with an e.e. of 30%. Ratios: [substratum]/[cat.] = 1000; [KOH]/[cat.] = 1.8.

EXAMPLE 34

12.2 mg ($2 \times 10^{-5}$ moles) of [Ir(PPEI)COD]$^+$ClO$_4^-$ (+) were suspended in 50 ml of isopropanol and oxidized with air for 4 hours. The resulting solution was degasified for 20 minutes at reflux in a nitrogen stream and then treated with 1.88 ml of a deaerated isopropanol solution of KOH (4 mg of KOH). The solution, after a preliminary 30-minute reduction in a nitrogen stream, was treated with 2.56 ml of deaerated propiophenone. After 150 minutes a conversion to phenylpropanol (+) of 96.6% with an e.e. of 26.1% was obtained. Ratios: [substratum]/[cat.] = 1000; [KOH]/[cat.] = 3.56.

EXAMPLE 35

12.2 mg ($2 \times 10^{-5}$ moles) of [Ir(PPEI)COD]$^+$ClO$_4^-$ (+) were suspended in 50 ml of isopropanol and oxidized with air for 4 hours. The resulting solution was degasified for 20 minutes at reflux in N$_2$ and then treated with 4.5 ml of a deaerated isopropanol solution of KOH (8 mg of KOH). The solution, after a preliminary 30-minute reduction in a nitrogen stream, was treated with 2.56 ml of deaerated propiophenone. After a 120-minute reaction, a conversion to phenylpropanol (+) of 93.3% with an e.e. of 26.1% was obtained. Ratios: [substratum]/[cat.] = 1000; [KOH]/[cat.] = 7.2.

EXAMPLE 36

6.1 mg ($1 \times 10^{-5}$ moles) of [Ir(PPEI)COD]$^+$ClO$_4^-$ (+) were suspended in 50 ml of isopropanol and oxidized with air for 4 hours. The yellow solution obtained was then degasified at reflux in a nitrogen stream for 20 minutes and then treated with 4.0 ml of an isopropanol solution of KOH (4 mg of KOH). The solution, after a preliminary reduction for 30 minutes at reflux in a nitrogen flow, was treated with 2.56 ml of deaerated propiophenone. After 180 minutes, a conversion to phenylpropanol (+) of 89.3% with an e.e. of 26.1% was obtained. Ratios: [substratum]/[cat.] = 2000; [KOH]/[cat.] = 3.56.

EXAMPLE 37

12.2 mg ($2 \times 10^{-5}$ moles) of [Ir(PPEI)COD]$^+$ClO$_4^-$ (+) were suspended in 50 ml of isopropanol and oxidized with air for 4 hours. The resulting yellow solution was then degasified at reflux for 20 minutes in a nitrogen flow and successively treated with 4.4 ml of a deaerated isopropanol solution of KOH (4 mg of KOH), effecting a preliminary reduction for 30 minutes at reflux in N$_2$. 3.0 ml of deaerated isobutyrophenone was then added to the solution. After 120 minutes a conversion to phenylisopropylcarbinol (+) of 92.1% with an e.e. of 13% was obtained. Ratios: [substratum]/[cat.] = 1000; [KOH]/[cat.] = 3.56.

EXAMPLE 38

11 mg ($2 \times 10^{-5}$ moles) of [Rh(PPEI)NBD]$^+$PF$_6^-$ (−) in 50 ml of isopropanol were oxidized with air for 12 hours. The resulting yellow solution was degasified for 15 minutes at reflux in a nitrogen stream and then treated with 3.5 ml of a deaerated isopropanol solution of KOH (5 mg of KOH). After heating at reflux in N$_2$ for 15 minutes, 2.4 ml of deaerated acetophenone were added. After 150 minutes, the conversion to phenylethanol (+) was of 40% with an e.e. of 5%. Ratios: [substratum]/[cat.] = 1000; [KOH]/[cat.] = 4.5.

We claim:

1. A process for catalytically reducing carbonyl compound by transfer of hydrogen from alcohols to aliphatic, alicyclic, aromatic homo- and heterocyclic ketones or aldehydes, catalyzed by complexes of rhodium or of iridium, comprising the reaction of a primary or secondary alcohol of formula (I) or a glycol:

with a ketonic compound of formula (II):

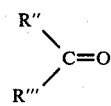

in which R and R' and respectively R'' and R''', also linked with each other according to homo- or heterocycles, are indifferently a hydrogen atom or a hydrocarbyl group having up to 30 atoms of carbon, provided that at least one of the symbols R'' and/or R''' is different respectively from R and/or R', in the presence of a complex catalyst of rhodium or of iridium selected from those having formulas (III) and (IV):

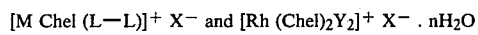

in which:
M is selected from Rh and Ir;
Chel is a chelating bidentate nitrogenous compound;
L-L is a molecule of a diolefin, or two molecules of a monoolefin;
X$^-$ is an anion selected from Cl$^-$, Br$^-$, J$^-$, FF$_6^-$, BF$_4^-$, ClO$_4^-$, B(C$_6$H$_5$)$_4^-$;
Y is a halogen; and
n is an integer from 0 to 3;
and in the presence of a compound selected from among mineral alkalis, at a temperature ranging from about 20° C. to the boiling temperature of the reaction mass.

2. A process according to claim 1, characterized in that the mineral alkali is a mineral alkaline compound selected from NaOH, KOH, LiOH, NaHCO$_3$ in a molar ratio to the catalyst of from 0.1 to 200 moles per 1 mole of catalyst.

3. A process according to claim 1, characterized in that the tertiary amine is selected between triethylamine and dimethyl-benzylamine in a molar ratio of from 0.1 to 200 per 1 mole of catalyst.

4. A process according to claims 1 or 2, characterized in that it is conducted in a medium selected from the alcohol and the glycol donor in excess and a compound selected from amongst toluene, benzene, methanol and water, optionally in admixture with one another, preferably from the alcohol or glycol donor.

5. A process according to claim 1, characterized in that the catalyst of formula (IV):

$$[Rh\ (Chel)_2Y_2]^+ X^- \cdot nH_2O \qquad (IV)$$

wherein the symbols have the meanings specified in claim 1, is activated by heating in the reaction medium in the presence of the mineral alkaline compound.

6. A process according to claim 1, characterized in that the catalyst of formula (III):

$$[M\ Chel\ (L\text{-}L)]^+ X^- \qquad (III)$$

wherein the symbols have the meanings specified in claim 1, is activated by oxidation with oxygen or a source thereof, and by successive heating in the reaction medium in the presence of the mineral alkaline compound.

7. A process according to claim 1, characterized in that the chelating nitrogenous compound is selected from 2,2'-dipyridyl, 3,3'-dimethyl-2,2'-dipyridyl, 4,4'-dimethyl-2,2'-dipyridyl, 1,10-phenanthroline, 5,6-dimethyl-1,10-phenanthroline, 4,7-dimethyl-1,10-phenanthroline, 3,4,7,8-tetramethyl-1,10-phenanthroline, 2-pyridinalphenylethylimine, 4,7-diphenyl-1,10-phenanthroline, 2-pyridinalnaphthylethylimine.

8. A process according to claim 1, characterized in that the chelating nitrogenous compound is a compound selected from those having formulas (V) and (VI):

(V), (VI)

in which groups $R^{iv}$ and $R^v$, like or unlike each other, optionally linked according to homo- and heterocycles, are respectively selected from amongst H, alkyls and aryls and from amongst OH, NH$_2$, alkyls and aryls, all having up to 30 carbon atoms, also containing functional groups selected from amongst carboxyls, esters and amides.

9. A process according to claims 1 to 8, characterized in that the prochiral ketonic compounds are reduced to chiral alcohols by employing chiral alcohols or glycols and/or catalysts of formula (III) as defined in claim 1, containing a chelating nitrogenous compound selected from those having formulas (V) and (VI) of claim 8.

10. A process according to claim 9, characterized in that the chelating nitrogenous compound is selected from pyridinalphenylethylimine and 2-pyridinalnaphthylethylimine.

11. A process according to claim 1, characterized in that in said complex catalyst L-L is a non-conjugated diolefin selected from 1,5-hexadiene, norbornadiene and 1,5-cyclooctadiene, or a monoolefin selected from cyclooctene and ethylene.

12. A process according to claim 1, characterized in that for 1 mole of carbonyl compound (II), from $1 \times 10^{-2}$ to $1 \times 10^{-6}$ moles of catalyst are employed.

13. A process according to claim 1, characterized in that the complex catalyst of rhodium or of iridium is prepared "in situ" in the reaction medium by adding the chelating compound to the halogenated olefinic complex of rhodium or of iridium.

14. A process according to claim 1, characterized in that the molar ratio between the reagents alcohol donor or glycol and carbonyl compound approximately ranges from 1:1 to 20:1.

15. A process according to claim 1, characterized in that the concentration of the carbonyl compound in the reaction medium approximately ranges from 10 to $10^{-3}$ moles per liter.

16. A process according to claim 1, characterized in that the catalyst concentration approximately ranges from $10^{-1}$ to $10^{-6}$ moles per liter of reaction mass.

17. A process according to claim 1, characterized in that the acceptor carbonyl compound is selected from amongst cyclohexanone, 4-terbutylcyclohexanone, 3-methyl-cyclohexanone, 4-methyl-cyclohexanone, 2-methyl-cyclohexanone, acetophenone, propiophenone, isobutyrophenone, dihydrocarvone, methyl-isobutylketone, benzaldehyde and p.methoxy-benzaldehyde, benzophenone, benzyl, dehydro-epiandrosterone acetate, and 3-oxosteroids.

18. A process according to claim 1, characterized in that the alcohol donor is selected from among isopropyl alcohol, 2-butyl alcohol, benzyl alcohol and ethyl alcohol.

19. A process according to claim 1, characterized in that the glycol donor is 1,2-cyclododecandiol.

20. A process according to claim 1, characterized in that the catalytic system contains an auxiliary component selected from the chiral amines.

21. The process of claim 1, in which the compounds having formulae I and II are substituted at R, R', R'' or R'''.

22. The process of claim 1, in which in said complex catalyst Y is Cl or Br.

* * * * *